United States Patent [19]
Van Woensel et al.

[11] Patent Number: 5,858,729
[45] Date of Patent: Jan. 12, 1999

[54] EXPRESSION OF PORCINE REPRODUCTIVE RESPIRATORY SYNDROME VIRUS POLYPEPTIDES IN THE SAME CELL

[75] Inventors: Petrus Alphonsus Maria Van Woensel, Boxmeer, Netherlands; Karl-Klaus Conzelmann, Bisingen, Germany

[73] Assignee: Akzo Nobel, N.V., Arnhem, Netherlands

[21] Appl. No.: 616,032

[22] Filed: Mar. 14, 1996

[30] Foreign Application Priority Data

Mar. 14, 1995 [EP] European Pat. Off. .............. 95200609

[51] Int. Cl.⁶ .......................... C12P 21/04; C12P 21/02; C12P 21/06; C12N 15/00

[52] U.S. Cl. ...................... 435/71.1; 435/69.1; 435/69.3; 435/320.1; 424/185.1; 424/204.1; 424/199.1; 935/32; 530/395; 530/403

[58] Field of Search .................... 435/320.1, 236, 435/237, 239, 235.1, 5, 173.3, 69.1, 71.1, 69.3; 530/395, 403; 935/32; 424/185.1, 204.1, 199.1

[56] References Cited

FOREIGN PATENT DOCUMENTS

| | | |
|---|---|---|
| 0319944 | 6/1989 | European Pat. Off. . |
| WOA 8802030 | 3/1988 | WIPO . |
| WO 93/14196 | 7/1993 | WIPO . |
| WOA 9428421 | 12/1994 | WIPO . |

OTHER PUBLICATIONS

J.J.M. Meulenberg et al., *Virology*, 206:1:155–183, Jan. 1995.

C. Delenda et al., *Archives of Virology*, 139(1–2) :197–207, 1994.

J. Kwang et al., *J Vet Diagn Invest*, 6:293–296 (1994).

J. Conzelmann et al., *Virology*, 1:329–339, 1993.

D.J. Davidson et al., *Biochemistry*, 29(23) :5548–5590, 1990.

J.B. Katz et al., *Veterinary Microbiology*, 44:1:65–76, Apr. 1995.

Overton et al. "The Protease and gag Gene Products of the Human Immunodeficiency Virus:Authentic Cleavage and post Translational Modification in an Insect Cell Expression System". Virology. vol. 170:107–116, 1989.

*Primary Examiner*—Marian C. Knode
*Assistant Examiner*—Datquan Lee
*Attorney, Agent, or Firm*—Mary E. Gormley

[57] ABSTRACT

The present invention provides a process for the recombinant DNA production of a mature form of the PRRSV ORF 3 or ORF 4 protein. This is achieved by the co-expression of the PRRSV ORF 2, ORF 3 and ORF 4 proteins by the same cell.

12 Claims, 3 Drawing Sheets

EXPRESSION OF PORCINE REPRODUCTIVE RESPIRATORY SYNDROME VIRUS POLYPEPTIDES IN THE SAME CELL

FIELD OF THE INVENTION

The present invention is concerned with a process for the preparation of a glycosylated form of PRRSV ORF 3 or ORF 4 protein, a host cell or vector virus for use in this process, a DNA molecule encoding said ORF 3 or ORF 4 protein, a glycosylated form of said ORF 3 or ORF 4 protein and a vaccine comprising said ORF 3 or ORF 4 proteins.

BACKGROUND OF THE INVENTION

The porcine reproductive respiratory syndrome virus (PRRSV) is the cause of a new porcine disease that has attacked over 5.000 North European pig farms since late 1990. This disease now called Porcine Reproductive Respiratory Syndrome (PRRS) is also known as Mystery Swine Disease. First, identified in Germany in December of 1990, the problem became increasingly critical in the beginning of 1991. In January and February of 1991 the disease spread to the Netherlands and Belgium. Outbreaks have also been reported from Spain. It is anticipated that the disease will become very costly from an economic standpoint, comparable to or even worse than Aujeszky's Disease.

The principal clinical signs in sows are anorexia and late abortion up to day 110 of pregnancy. With piglets a high incidence of stillborn and/or weak piglets in addition to respiratory problems are observed. In fatteners chronic pneumonia and increased mortality occur.

In order to develop a vaccine to protect pigs against PRRS or to develop a diagnostic method to determine infection in pigs, the causative agent of the disease has to be identified, isolated and made suitable as an immunogen in a vaccine or antigen in a diagnostic assay.

Conventional vaccines may comprise chemically inactivated virus vaccines or modified live-virus vaccines. However, inactivated vaccines require additional immunizations, disadvantageously contain adjuvants, are expensive to produce and are laborious to administer. Furthermore, some infectious virus particles may survive the inactivation process and cause disease after administration to the animal.

In general, attenuated live virus vaccines are preferred because they evoke an immune response often based on both humoral and cellular reactions. Up to now, such vaccines based on PRRSV strains can only be prepared by culturing and serial passaging of virulent strains in macrophage cell culture. However, because of this treatment uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals. Furthermore, culturing of the PRRSV strain on a macrophage cell line is very laborious and results in a pour yield of the virus.

Improved vaccines, both live- and subunit vaccines, may be constructed based on recombinant DNA technology. These vaccines would only contain the necessary and relevant PRRSV immunogenic material capable of eliciting an immune response against the PRRSV pathogens, or the genetic information encoding said material, and not display above-mentioned disadvantages of the live or inactivated vaccines.

The causative agent of the disease is now known to be a small enveloped RNA virus, and the European type of this virus has been described by Wensvoort et al. (The Vet. Quarterly 13, 121–130, 1991). Its relatedness to Lactate Dehydrogenase-elevating virus (LDV) and Equine Arteritis virus has been described by Conzelmann et al. (Virology 193, 329–339, 1993), and by Meulenberg et al. (Virology 192, 62–72, 1993), thus placing the virus in the group of Arteriviridae.

A strain of this European type, called the "Lelystad virus" (LV) has been deposited with the Institut Pasteur, Paris, France under nr. I-1102, in connection with PCT WO 92/21375 by the Central Veterinary Institute, Lelystad, The Netherlands.

Another European strain has been described in EPA no. 91.202.646.5, and was deposited with the Collection Nationale de Cultures de Micro-organismes (CNCM) of the Institut Pasteur at Paris France under nr. I-1140.

This European strain has recently been described by Conzelmann et al. (Virology 193, 329–339, 1993).

The American type of the virus has been described by Benfield et al. (J. Vet. Diagn. Invest. 4, 127–133, 1992). A strain of the American type has been deposited with the ATCC under nr. VR-2332, and is mentioned in PCT WO 93/03760 and European Patent Application 0.529.584. An important observation was made by Wensvoort et al. (J. Vet. Diagn. Invest. 4, 134–138, 1992), early after the virus was found, when he compared American and European strains on the basis of their antigenic characteristics and demonstrated that the European and American strains display considerable antigenic differences.

The genomes of two European strains of PRRSV and parts of the genomes of US isolates have been molecularly cloned and sequenced (PCT WO 92/21375; Meulenberg et al., Virology 192, 62–72, 1993; Conzelmann et al., supra; Kwang et al., J. Vet. Diagn. Invest. 6, 293–296, 1994; Mardassi et al., J. Gen. Virol. 75, 681–685, 1994; Meng et al., Proc. 13th IPVS Congress, 61, 1994).

The RNA of the PRRSV genome comprises about 15 kb and 8 open reading frames (ORFs) can be identified therein, ORF 1A,B and ORFs 2 to 7. ORF 1A,B encodes a.o. the viral RNA polymerase, whereas the ORFs 2 to 6 encode the viral membrane (envelope) proteins. ORF 7 encodes the nucleocapsid protein. In infected cells a 3' coterminal nested set of six major subgenomic mRNAs can be demonstrated in both the European and US isolates (Meng et al., supra). Table 1 summarizes the characteristics of the ORFs encoding the structural proteins of PRRSV (Conzelmann et al., supra).

TABLE 1

| ORF | mRNA (kb) | Amino acids | Calculated MW protein (kD) |
| --- | --- | --- | --- |
| 2 | 3.7 | 249 | 28.4 |
| 3 | 3.1 | 265 | 30.6 |
| 4 | 2.6 | 183 | 20.0 |
| 5 | 2.0 | 201 | 22.4 |
| 6 | 1.4 | 173 | 18.9 |
| 7 | 0.9 | 128 | 13.9 |

The distribution of the ORFs on the PRRSV genome is shown in FIG. 1 and corresponds to that found by Meulenberg et al. (supra).

Little is known about the PRRSV proteins expressed by the ORFs mentioned before. 5 viral proteins of about 15–26 kD were identified in lysates of cells inoculated with an European or US PRRS isolate (Nelson et al., J. Clin. Microbiol. 31, 3184–3189, 1993 and Benfield et al, Proc. 13th IPVS Congress, 62, 1994). It was demonstrated that the ORF 7, ORF 6 and ORF 5 proteins are present in virions (Meulenberg et al., Virology 206, 155–163, 1995). It has been found now that two different forms, a small and a large form, of the ORF 3 and ORF 4 protein are present in cells infected with PRRSV, but only one form is present in purified virions isolated from the supernatant of infected cells. The two forms of each ORF protein are distinguished by the level of processing of their carbohydrate chains. The large forms, which are the forms present in the purified virions, are Endoglycosidase H (Endo-H) resistant, whereas the small forms are Endo-H sensitive. The substrate of the enzyme Endo-H is only the "high-mannosylated" form of the glycoproteins. This enzyme cleaves the oligosaccharide chain immediately after the carbohydrate group GlcNac which is coupled to the amino acid asparagin (Asn). More complex forms, i.e. forms in which the glycosylation process is complete, are resistant to Endo-H cleavage. The Endo-H resistance was used herein to determine the stage of the glycosylation process of the ORF 3 and 4 proteins and to distinguish the small ("high-mannose") forms of the ORF proteins from the large ("complex") form thereof. The enzyme Peptid-N-Glycohydrolase (PnGase-F) was used to obtain the completely deglycosalyted form (polypeptide backbone) of ORF 3 and 4. It was found that the ORF 3 and 4 glycoproteins incorporated in virons are the large ("complex") forms which resulted from their precursor small ("high mannose") forms by further processing, as a result of which said large forms became Endo-H resistant. The molecular weight (mw) as determined by SDS-PAGE of the ORF 3 and ORF 4 protein forms is shown in Table 2.

TABLE 2

| ORF | MW non-glycosylated form (kD) | MW small[1] form (kD) | MW large[2] form (kD) |
| --- | --- | --- | --- |
| 3 | 26 | 41–44 | 55–60 |
| 4 | 15,5 | 32–35 | 40–47 |

[1]Endo-H sensitive
[2]Endo-H resistant

After expression of individual ORFs in eukaryotic cells transformed with the individual ORFs it was found that, in contrast to virus infected cells, exclusively the small forms of the ORF 3 and ORF 4 proteins were produced. Since the individual proteins are not completely processed in eukaryotic cells, most likely the transport of the proteins from the endoplasmic reticulum to the medial cisternae of the golgi apparatus is not possible. Surprisingly, it has been found now that in order to obtain the large forms of the PRRSV ORF 3 and ORF 4 proteins, co-expression of ORF 2, ORF 3 and ORF 4 in one cell is required and sufficient. During the infection process, animals are confronted with the mature (large) forms of the proteins. Therefore, the present invention provides a process for the recombinant DNA preparation of the mature large forms of PRRSV ORF 3 and ORF 4 proteins.

SUMMARY OF THE INVENTION

Therefore the present invention provides a process for the preparation of a glycosylated form of PRRSV ORF 3 or ORF 4 protein comprising the steps of culturing a suitable host cell transformed with a DNA fragment encoding the ORF 3 or ORF 4 protein, or a host cell infected with a vector virus harbouring a DNA fragment encoding the ORF 3 or ORF 4 protein, under conditions expressing the protein, and harvesting the expressed protein, characterized in that the same host cell simultaneously expresses PRRSV ORF 2, ORF 3 and ORF 4 proteins. ORF 2, ORF 3 and ORF 4 are defined as the large protein encoding (partially overlapping) regions down stream (3'-direction) of the polymerase encoding region ORF 1 as defined by the map showing the distribution of the ORFs on the PRRSV genome shown in FIG. 1. This map corresponds with that shown in Meulenberg et al. (supra) and is considered as a representative map for all PRRS viruses. ORFs 5–7 are also defined by their position on the maps mentioned before.

DETAILED DESCRIPTION OF THE INVENTION

In particular, the above-mentioned ORFs are characterized by the amino acid sequence of the PRRSV proteins encoded by the respective ORFs disclosed in Conzelmann et al. (supra).

It will be understood that for the particular ORF proteins natural variations can exist between individual PRRSV isolates. These variations may be demonstrated by the difference of one or more amino acid in the overall sequence. An example of such a variant PRRSV and the amino acid sequence of these ORF proteins is disclosed by Meulenberg et al. (supra).

Preferably the ORF proteins to be used in the present invention display a homology of at least 55%, more preferably at least 70% on the amino acid sequence level with the amino acid sequences disclosed by Conzelmann et al. (supra).

An essential aspect of the present invention is that one and the same host cell co-expresses the PRRSV ORF 2, ORF 3 and ORF 4 proteins. This can be achieved by transforming the host cell with a DNA fragment comprising the said three ORFs or by transforming the cell with more than one DNA fragment such that all three ORFs are introduced into the cell. For example, the host cell can be co-transformed three DNA fragments, the first comprising ORF 2, the second comprising ORF 3 and the third comprising ORF 4.

Similarly, the host cell may be (co-)infected by one vector virus or more vector viruses as long as the three ORFs mentioned above are introduced into the same cell.

Although the simultaneous expression in a host cell of ORF 2, ORF 3 and ORF 4 is required and sufficient in order to produce the large mature forms of the ORF 3 and ORF 4 protein, if desired also other ORFs of PRRSV, such as one or more of the ORFs 5–7, in particular ORF 5 and/or ORF 7, may be co-expressed by the said host cell.

Furthermore, in the process according to the invention all of ORF 2, ORF 3, and ORF 4 are under the transcriptional control of promoter sequences such that expression of said ORFs is guaranteed. Preferably each ORF is operatively linked to a separate promoter.

A DNA fragment to be used in the present invention may comprise various replication effecting DNA sequences with which the ORF is not associated or linked in nature, resulting in a so called recombinant nucleic acid molecule which can be used for the transformation of suitable host. Such hybrid DNA molecules, are preferably derived from, for example plasmids. Specific vectors which can be used to clone the PRRSV ORFs are known in the art and include inter alia plasmid vectors such as pBR322, various pUC, pGEM and Bluescript plasmids (see also Rodrigquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of such a recombinant nucleic acid molecule are known to those of ordinary skill in the art and are inter alia set forth in Maniatis, T. et al. (Molecular Cloning A Laboratory Manual; Cold Spring Harbor Laboratory, 2nd edition, 1989).

A suitable host cell is a cell which can be transformed by a DNA fragment encoding a PRRSV ORF protein and which is able to express the PRRSV ORF protein in a glycosylated form. "Transformation", as used herein, refers to the introduction of a heterologous nucleic acid sequence into a host cell, irrespective of the method used, for example direct uptake or transduction. The heterologous nucleic acid sequence may be integrated into the host genome. For expression the heterologous DNA fragment is provided with appropriate expression control sequences that are compatible with the designated host and can regulate the expression of the inserted nucleic acid sequence.

The host preferably is of eukaryotic origin such as a yeast, e.g. *Saccharomyces cerevisiae* or a higher eukaryotic cell such as an insect, plant or mammalian cell, including HeLa cells and Chinese hamster ovary (CHO) cells. Insect cells include the Sf9 cell line of *Spodoptera frugiperda* (Luckow et al., Bio-technology 6, 47–55, 1988). Information with respect to the cloning and expression of the PRRSV ORFs in eukaryotic cloning systems can be found in Esser, K. et al. (Plasmids of Eukaryotes, Springer-Verlag, 1986).

When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV-40 promoter (Berman, P. W. et al., Science 222, 524–527, 1983) or, e.g. the methallothionein promoter (Brinster, R. L., Nature 296, 39–42, 1982) or a heat shock promoter (Voellmy et al., Proc. Natl. Acad. Sci. USA 82, 4949–53, 1985).

Alternatively, a suitable host cell is a cell which is susceptible for infection by a vector virus harbouring a DNA fragment encoding the PRRSV ORFs. In the vector virus the heterologous DNA fragment is inserted into a non-essential region of the virus, i.e. a region which can be used for the incorporation of said DNA fragment without disrupting essential functions of the virus such as those necessary for infection or replication of the virus. Such regions are generally known in the art for various viruses including herpesviruses and pox viruses.

To obtain large quantities of PRRSV ORF proteins the preferred expression system is the baculovirus expression system (BVES). In this system insect cells like *Spodoptera furgiperda* (Sf; IPLB-Sf21) cells are kept in cell culture as host for a baculovirus, like an *Autographa californica* nuclear polyhedrosis virus (AcNPV). Some of the genes in AcNPV are expressed to high levels, but are non-essential to the viral infection-cycle. These genes are the target for homologous recombination in transfected cells, between a baculo-transfer plasmid like pAcAS3 and wildtype (wt) AcNPV DNA. In pAcAS3 (J. Vlak et al., Virology 179, 312–320, 1990) heterologous genes are inserted downstream of the p10 promoter instead of the non-essential p10 gene, surrounded by sequences of wt AcNPV that target the recombination process. To facilitate screening for recombinants, pAcAS3 also contains the LacZ gene, causing recombinant plaques to turn blue upon addition of X-gal to the medium.

In the claimed process the host cells defined above can be cultured under conditions which are favourable for the expression of the PRRSV ORF 2, ORF 3 and ORF 4 proteins. Vaccines or diagnostic assays may be prepared using samples of the crude culture, host cell lysates or host cell extracts, although in another embodiment more purified ORF 3 or ORF 4 proteins may be prepared depending on its intended use. In order to purify the proteins produced, host cells expressing both ORF 2, ORF 3 and ORF 4 are cultured in an adequate volume and the proteins produced are isolated from such cells or from the medium if the proteins are excreted. Proteins excreted into the medium can be isolated and purified by standard techniques, e.g. salt fractionation, centrifigation, ultrafiltration, chromatography, gel filtration immuno precipitation or immuno affinity chromatography, whereas inter cellular proteins can be isolated by first collecting said cells, disrupting the cells, for example by sonication or by other mechanically disruptive means such as French press, followed by separation, if desired, of the proteins from the other inter cellular components. Cell disruption could also be accomplished by chemical (e.g. EDTA treatment) or enzymatic means such as lysozyme digestion.

According to a further embodiment of the invention a vector virus is provided said vector virus harbouring one or more heterologous DNA fragments, characterized in that the DNA fragment(s) encode PRRSV ORF 2, ORF 3 and ORF 4 protein. Such a vector virus has already been described above in a general sense. This vector virus can be used in a new approach to vaccine development, i.e. the expression of genes of foreign pathogens using live attenuated viral vaccine strains as carrier (viral vaccine vectors). Expression of antigen by a live vector virus may mimic expression after natural infection and may stimulate both humoral and cellular immune responses. Such vectors may be used for immunization against diseases for which no adequate vaccines are currently available, or which cannot be safely or easily produced. As outlined above it has been found that the expression of immunogens by a vector virus harbouring PRRSV ORF 3 or ORF 4 only mimics natural infection if the vector virus according to the present invention is applied.

Virus vectors suited for the simultaneous expression of PRRSV ORF 2, ORF 3 and ORF 4 are known to those skilled in the art and include pox viruses, such as vaccinia (Piccini and Paoletti, Adv. Vir. Res. 34, 43–64, 1988; Riviere et al., J. Virol. 66, 3424–3434, 1992, Mengeling et al., Arch. Virol. 134, 259–269, 1994), swinepox (van der Leek et al., The Vet. Record 134, 13–18, 1994), adenovirus (Hsu et al., Vaccine 12, 607, 1994) and herpesviruses, such a pseudorabies virus.

Preferred vector viruses to be used in the present invention are derived from pseudorabies viruses (PRV).

For example, for PRV several non-essential regions have been disclosed and used for the incorporation of heterologous DNA sequences, such as the genes encoding gp50, gp63, gI, gIII, gX, 11K, thymidine kinase (TK), ribonucleotide reductase (RR), protein kinase (PK) or 28K (Peeters et al., J. Virol. 67, 170–177, 1993; de Wind, N. et al., J. Virol 64, 4691–4696, 1990; Moorman, R. J. M. et al., J. Gen Virol 71, 1591–1595, 1990; Petrovskis, E. A. et al., Virology 159, 193–195, 1987; van Zijl, M. et al., J. Gen. Virol 71, 1747–1755, 1990; Thomsen, D. R. et al., Gene 57, 261–265, 1987; Keeler, C. L. et al., Gene 50, 215–224, 1986; Whealey, M. E. et al., J. Virol 62, 4185–4194, 1988; van Zijl, M. et al., J. Virol 65, 2761–2765, 1991; Mettenleiter, Th. C. et al., Virology 179, 498–503, 1990; U.S. Pat. No. 4,609,548, European patent no 0263207, European patent application no. 94203643 and PCT application WO/94/01573).

Well-known procedures for inserting DNA sequences into a cloning vector and in vivo homologous recombination or cosmid cloning techniques can be used to insert the ORFs into the non-essential region of the herpesvirus genome (Maniatis, T. et al., in "Molecular cloning", Cold Spring Harbor Laboratory, 1989; European patent application no. 074808; Roizman, B. and Jenkins, F. J., Science 229, 1208, 1985; Higuchi, R. et al., Nucleic Acids Res. 16, 7351, 1988, de Wind, N. et al., J. Virol. 64, 4691–4696, 1990; van Zijl, M. et al., J. Virol. 62, 2191–2195, 1988; Ackermann, M., J. Vet-Med. B., 35, 379–396, 1988, and methods described in the paragraph above).

The DNA fragments encoding the PRRSV ORF 2, ORF 3 or ORF 4 proteins may be inserted in the same or different regions of the vector virus genome.

As a matter of course the invention also provides a mixture of two or more, preferably two or three, vector viruses, said mixture being able to co-infect a host cell in vivo such that the PRRSV ORF 2, ORF 3 and ORF 4 proteins are simultaneously expressed in vivo by the same cell. This mixture may also be used as an active component in a vaccine. In case the mixture comprises two vector viruses, one virus harbours two of the three ORFs mentioned above and the second virus harbours the third required ORF. In case the mixture comprises three vector viruses, each virus harbours one of the required ORFs. If desired, one or more of the vector viruses in the mixture harbours one or more of the ORFs 5–7 of PRRSV.

Preferably, the vector virus to be incorporated in said mixtures is derived from a PRV vaccine virus, preferably a PRV strain is used which is genotypically gD⁻ (and if desired phenotypically gD⁺) and/or gE⁻ (PCT application WO 94/01573, EP application no. 94203643).

A vector virus according to the invention or the vector viruses to be incorporated into the mixture described above, can be prepared by culturing a host cell infected with the vector virus, whereafter virus containing cells and/or vector viruses grown in the cells can be collected, optionally in a pure form, and incorporated in a vaccine optionally in a lyophilized form or used in a diagnostic assay.

The invention further provides a DNA fragment comprising a nucleic acid sequence encoding PRRSV ORF 2, ORF 3 and ORF 4 protein wherein each ORF encoding the said proteins is operatively linked to a promoter. Such a DNA fragment can be used for the preparation of a host cell or vector virus defined above.

Also included within the scope of the present invention are a purified Endo-H resistant PRRSV ORF 3 or ORF 4 protein. A preferred form of the Endo-H resistant ORF 3 or ORF 4 protein has a molecular weight of 55–60 kD or 40–47 kD, respectively.

These Endo-H resistant ORF proteins may be provided in a substantial pure form, free of PRRSV material with which these are normally associated in nature or as a mixture of PRRSV proteins obtained by the process according to the present invention.

Furthermore, the present invention provides a vaccine which induces an effective immune response in pigs against a PRRS virus. This vaccine can be a sub-unit vaccine comprising the ORF 3 and/or ORF 4 proteins produced by the process according to the invention together with a pharmaceutical acceptable carrier our diluent.

Alternatively, a vector vaccine is provided comprising the vector virus according to the invention or a mixture of vector viruses as defined above together with a pharmaceutical acceptable carrier or diluent.

For example, the vaccine may also contain an aqueous medium or a water containing suspension, often mixed with other constituents, e.g. in order to increase the activity and/or shelf life. These constituents may be salts, pH buffers, stabilizers (such as skimmed milk, casein hydrolysate or citric acid) or preservatives such as thimerosal, merthiolate and gentamycin.

If desired, the vaccine according to the invention is formulated with one or more adjuvants. Suitable examples are saponins such as Quil A, aluminium hydroxide, cholera- or tetanus toxoid, oil emulsion (o/w or w/o) and aqueous vitamin-E dispersion.

The vaccine according to the invention can be administered in a conventional active immunization scheme: single or repeated administration in a manner compatible with the dosage formulation and in an amount that will be prophylactically and/or therapeutically effective and immunogenic. The administration of the vaccine can be done, e.g. intradermally, subcutaneously, intramusculary, intraperitonally, intravenously, intranasally or orally.

The invention also relates to an "immunochemical reagent", which reagent comprises at least one of the PRRSV ORF 3 or ORF 4 proteins produced according to the process of the invention.

The term "immunochemical reagent" signifies that said proteins have been bound to a suitable support or have been provided with a labelling substance.

The supports which can be used are, for example, the inner wall of a microtest well or cuvette, a tube or capillary, a membrane, filter, test strip or the surface of a particle such as, for example, a latex particle, an erythrocyte, a dye sol, a metal sol or metal compound as sol particle.

Suitable labelling substances are, inter alia, a radioactive isotope, a fluorescent compound, an enzyme, a dye sol, metal sol or metal compound as sol particle.

The "immunochemical reagent" can be used, in a diagnostic assay wherein said reagent is incubated with a sample suspected of containing anti-PRRSV antibodies after which the presence or absence of the antibodies is determined.

The invention also relates to a test kit to be used in an immuno-assay, this test kit containing at least one immunochemical reagent according to the invention.

The immunochemical reaction which takes place using this test kit is preferably a sandwich reaction, an agglutination reaction, a competition reaction or an inhibition reaction.

EXAMPLE 1

Transient simultaneous expression of PRRSV ORFs in the same cell by vaccinia virus The preparation and analysis of cDNA clone pRRSV-T1 from PRRSV was described in Conzelmann et al., (supra). Fragments containing the entire ORFs of PRRSV and starting close to the respective ATG initiation codon were cloned downstream of the T7 promoter of the vector pBluescript SKII- (Stratagene) into the EcoRV restriction site (ORFs 2 and 5) or SmaI restriction site (ORFs 3 and 4) after treatment with Klenow polymerase. The inserts contained the following PRRSV-T1 sequence residues (Conzelmann et al.; supra):

| ORF 2: | (EcoRI-NdeI, Klenow fill in) | 1602–2381 |
|---|---|---|
| ORF 3: | (HincII-HinfI, Klenow fill-in) | 2207–3040 |
| ORF 4: | (BstYI-SpeI, Klenow fill-in) | 2673–4920 |
| ORF 5: | (BstXI-HindIII, Klenow fill in) | 3304–3954 |

Transfection experiments were carried out in BHK-21 (Baby Hamster Kidney) cells, clone BSR after infection at an m.o.i. of 5 with vTF7-3 (Fuerst et al., 1986, PNAS 83, 8122–8126) expressing T7 RNA Polymerase. One hour postinfection cells were transfected with 2 µg of plasmids by using the Stratagene "mammalian transfection kit" according to the manufactures instructions.

Cells were washed four hours after transfection with methionin-free medium. After starvation for 30 min. 50 µCi of Tran(35S)-label per dish was added and the cells were incubated for 24 hours at 37° C. Cells were washed with PBS, lysed in 1% Triton and proteins were denaturated by 95° C. and 2% SDS.

Crude protein samples were precipitated with anti ORF 4 monoclonal antibody (mab35) and fixed *Staphylococcus aureus* cells according to Kessler (Methods Enzymol. 73, 442–459, 1981). The immune complexes were collected by centrifugation. The resulting pellets were resuspended in 30 µl Laemmili sample buffer and incubated for 5 min. at 95° C. After centrifugation the supernatants were analysed in SDS- 10% polyacrylamid gels. Gels were fixed, impregnated with En3Hance, dried on Whatman 3 MM filter paper and exposed at −70° C. to KodakX-AR5 films.

Deglycosylation of the expressed proteins by Endo-H was carried out as follows: The precipitated and washed immune complexes were re-suspended in NEB-buffer (New England Biolabs). 1.5 Units of Endo-H was added and the sample was incubated for 16 hours at 37° C., and subsequently re-suspended in 30 µl Laemmili sample buffer for SDS-PAGE analyses.

In a first experiment (FIG. 2) co-expression of several ORF combinations was carried out. It is demonstrated that co-expression of ORF 2, ORF 3 and ORF 4 is required and sufficient to support the expression of the mature large form of ORF 4 (40–47 kD). In order to demonstrate that the observed molecular weight form of the ORF 4 protein is similar to that present in virions, deglycosylation experiments with Endo-H were performed on expression products of different combinations (FIG. 3). It is shown that only cells co-transformed with ORF 2, ORF 3 and ORF 4 express the large form of the ORF 4 protein, and that these large forms are resistant to Endo-H treatment.

EXAMPLE 2

Mixture of PRV vector viruses expressing ORF 2, 3 and 4 of PRRSV

Construction of PRV $gD^-$ and $gE^-$ vector virus.

From the PRV NIA-3 strain the gD containing PstI NcoI fragment was subcloned in the PGEM5ZF(+) vector. With the TRANSFORMER procedure (clonetech) Spe I and AvrII restriction sites were introduced. The SpeI site was introduced at 17 nucleotides upstream of the ATG start codon of the gD. The AvrII site was introduced at the first nucleotide after the TAG stop codon. After these mutations had been introduced, the complete gD gene was removed by restriction enzyme digestion with SpeI and AvrII. On the former gD site an oligo nucleotide was inserted containing the SpeI, EcoRI, EcoRV, HindIII, and the AvrII restriction sites. Then the PstI-NcoI fragment was isolated from the plasmid and used for homologous recombination with the PRV R1 strain (de Wind et al., J. Virology 64, 4691–4696, 1990) by the method described by Peeters et al. J. Virology 66, 894–905, 1992).

To obtain a gD- and gE-negative mutant the NdeI-StuI fragment of the HindIII-B fragment of PRV was replaced with the NdeI-StuI fragment containing the gD-deletion. This HindIll fragment also contained a deletion encompassing gE (from DraI-site at position 6831 to linker-insertion site of mutant 324 (de Wind et al.,1990, supra) at position 8562). The resulting plasmid was then used to generate gD-, gE-virus by recombination with the wild type cosmids c-179, c-27 and c-443 (van Zijl et al., J. Virology 62, 2191–2195, 1988).

Construction of PRV gD mutants expressing ORF 2, 3 and 4 of PRRSV.

Each ORF was inserted separately in the pseudorabies gD-, gE-vector D57 described-above. The following strategy was used to obtain recombinant viruses. The ORFs were specifically amplified by using the polymerase chain reaction. The amplified products were then cloned into the pCR™II vector. Then the ORFs were isolated from this vector and cloned into the transfer vector pDHβ. This vector was then used to transfer the ORFs of PRRSV into the viral genome of the PRV D57 strain.

PCR amplification of the PRRSV ORFs

To amplify the specific ORFs the following primer pairs corresponding to the PRRSV sequences were used:

ORF 2:

Upper primer; nucleotides 1609–1628 inclusive

Lower primer; complementary sequence of nucleotides 2351–2370 inclusive

ORF 3:

Upper primer; nucleotides 2211–2230 inclusive

Lower primer; complementary sequence of nucleotides 3025–3044 inclusive

ORF 4

Upper primer; nucleotides 2747–2766 inclusive

Lower primer; complementary sequence of nucleotides 3296–3315 inclusive

All nucleotide numbers refer to the PRRSV sequence as provide by Conzelmann at. al. (Virology 193, 329–339, 1993)

The ORFs were amplified from a plasmid containing all structural genes of PRRSV (pPRRSV) by the following method:

The PCR mix was prepared by adding; 5 μl (10×) PCR buffer (purchased from the enzyme supplier), 5 μl (2 mM) dNTPs, 5 μl (10 μM) upper primer, 5 μl (10 μM) lower primer, 0.2 U Super Taq (Sepharo Q), 1 μl (1 μg/μl) pPRRSV and water to a total volume of 50 μl. After a drop of mineral oil had been placed on top of the mixture, PCR was performed using 30 cycles of 1 min at 94° C., 1 min at 55° C. and 1 min at 72° C. After amplification the products could be visualized on the 2% agarose gel containing 0.5 μg/ml ethidium bromide.

Cloning of amplified ORFs

Amplified products were cloned into the pCR™II vector using the Invitrogen TA cloning kit. All procedures were performed according the manufacturers instructions. From this vector the ORFs were cloned into the transfer vector pDHJβ. PCR products cloned in the right orientation (ATG starting codon ORF located at the side of the T7 promoter of the pCR™II vector) were removed from the vector by a BamHI digestion followed by Klenow treatment to generate blunt ends and thereafter a XbaI digestion. The products were separated on a 1% agarose gel and the band containing the ORF purified from the gel with Geneclean according the manufacturers instructions. The vector was digested first with EcoRI and thereafter with XbaI, separated on a gel and the linear vector purified with the use of Geneclean. All ORF containing fragments were ligated into the linearized vector using T4 ligase. All enzymes were purchased from Pharmacia and all methods were performed using standard techniques (Current Protocols in Molecular Biology).

Generation of PRV mutants containing PRRSV inserts

PRV virus with its gD and the gE gene deleted (D57 strain) was cultured on gD complementing Vero cells. At full CPE virus was harvested and its DNA extracted according to standard techniques. Viral DNA was cleaved with EcoRI using the unique EcoRI site located in the formal gD locus. The pDHβ vectors, containing the PRRSV inserts, were linearized with MluI. Both the linearized plasmid and the cut viral D57 DNA were mixed with DOTAP (Boehringer Manheim) according the manufacturers instructions. A total of 5 μg of DNA was mixed with 10 μl of DOTAP in a total volume of 500 μl 20 mM Hepes buffer. For the DNA a molar ratio of 10 copies of plasmid DNA to 1 copy of viral DNA was used. The mixture was incubated for 6 hours at 37° C. on a 80% confluent monolayer of the gD complementing Vero cells from which the medium had been removed. After this incubation period medium was added and the plates were further incubated at 37° C. At full CPE the medium was harvested. Finally, recombinant viruses were isolated from the harvested medium by limiting dilution and identified by the expression of the inserted PRRSV genes using immune fluorescence. A mixture of the vector viruses expressing the ORFs 2, 3 and 4 is prepared and used for immunisation of pigs.

Figure 1:
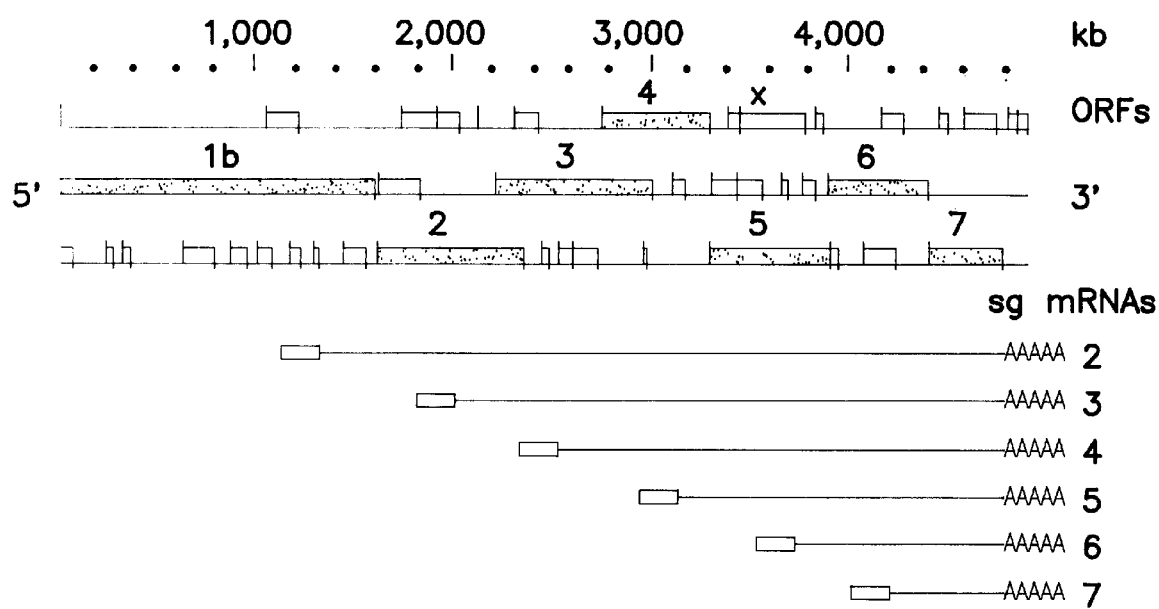
FIG. 1:
Distribution of open reading frames in the determined PRRSV sequence and location of subgenomic mRNAs (sg mRNAs, boxes represent the leader RNA).
Figure 2:
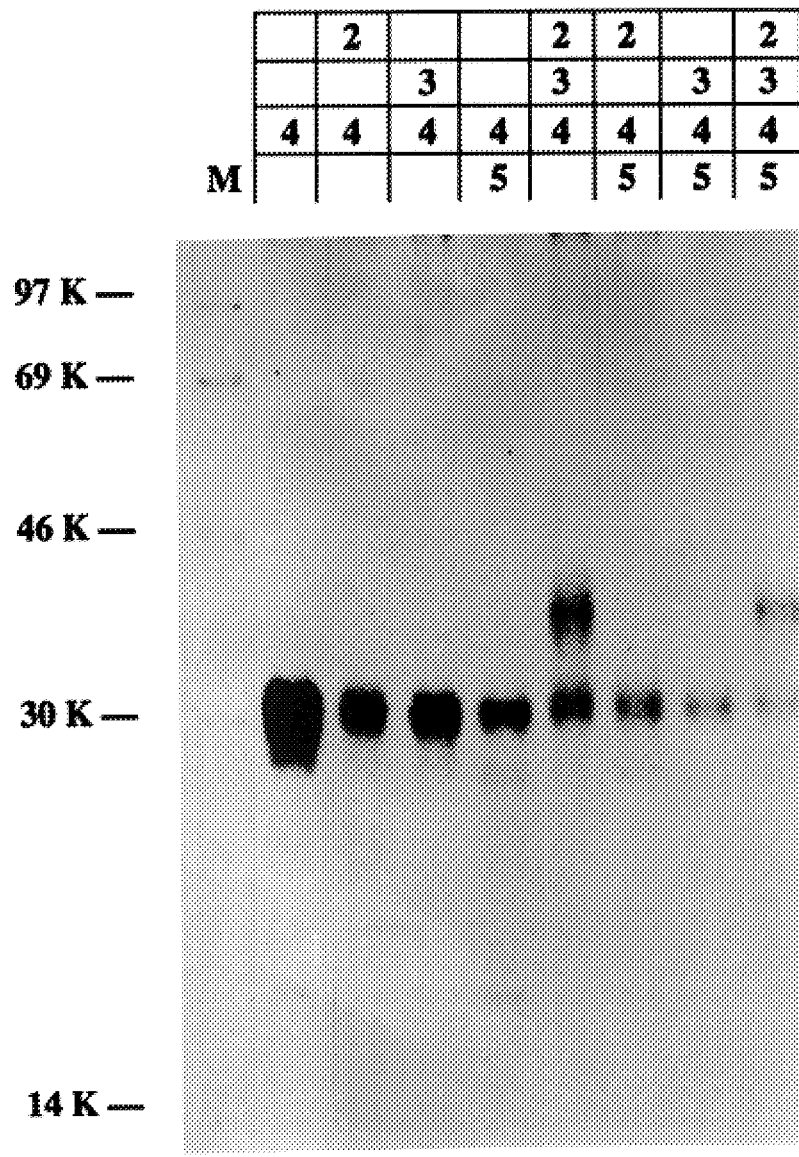
FIG. 2:
Radio-immunoprecipitation of transiently expressed PRRSV ORFs. The expressed proteins were separated on a 10% SDS-PA gel. The left lane comprises marker (M) proteins. The other lanes display the electrophoresis of labelled proteins expressed by the host cell transformed with the ORFs mentioned at the top.
Figure 3:
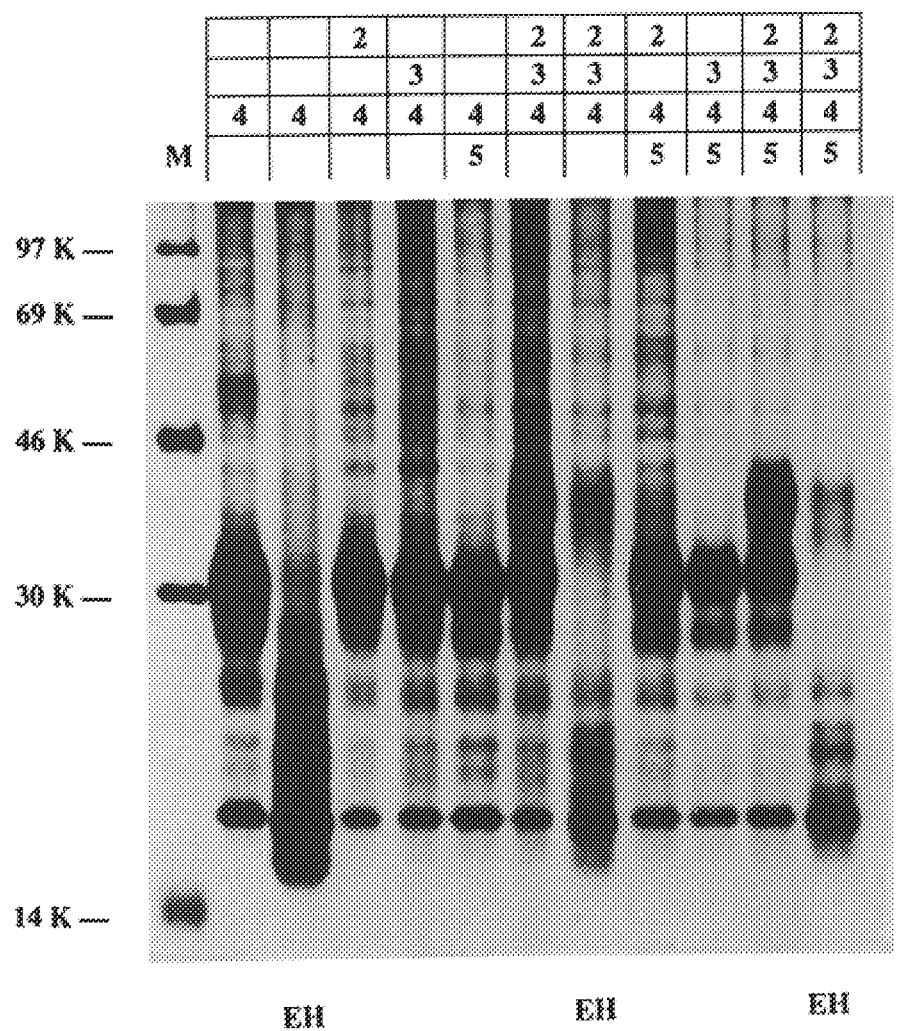
FIG. 3:
Same as FIG. 2. Additional some expression products were treated with Endo-H (EH).

We claim:

1. A process for the preparation of a glycosylated forms of porcine reproductive respiratory syndrome virus (PRRSV) ORF 3 and ORF 4 proteins, comprising the steps of:
    a. culturing a suitable host cell transformed with subgenomic DNA fragments encoding the PRRSV ORF 2, ORF 3 and ORF 4 proteins, or a suitable host cell infected with one or more vector (virus) viruses each of which comprise one or more subgenomic DNA fragments encoding the PRRSV ORF 2, ORF 3 or ORF 4 proteins, under conditions whereby the ORF 2, ORF 3 and ORF 4 proteins are expressed; and
    b. harvesting the expressed proteins.

2. The process according to claim 1, wherein said host cell comprises PRRSV ORF 2, ORF 3 and ORF 4 as a result of coinfection with more than one vector virus.

3. The process according to claim 2, wherein the vector virus is a baculovirus.

4. A host cell transformed with subgenomic DNA fragments encoding PRRSV ORF 2, ORF 3 and ORF 4.

5. A vector virus comprising two or more heterologous DNA fragments selected from the group consisting of the DNA fragments that encode PRRSV ORF 2, ORF 3 and ORF 4 proteins.

6. The vector virus according to claim 5, which is pseudorabies virus.

7. A mixture of two or more vector viruses, each vector virus comprising one or more subgenomic PRRSV ORFs, said mixture being able to co-infect a host cell and to express PRRSV ORF 2, ORF 3 and ORF 4 in the cell.

8. An isolated DNA molecule comprising a subgenomic nucleic acid sequence encoding PRRSV ORF 2, ORF 3 and ORF 4 proteins, each ORF being separately and operatively linked to a promoter.

9. An isolated, glycosylated, endo-H resistant form of PRRSV ORF 3 or ORF 4 protein.

10. An immunogenic composition comprising the ORF proteins produced by the process according to claim 1 together with a pharmaceutically acceptable carrier or diluent.

11. An immunogenic composition comprising at least one endo-H resistant PRRSV protein selected from the group consisting of ORF 3 and ORF 4, together with a pharmaceutically acceptable carrier or diluent.

12. An immunogenic composition comprising at least one vector virus that singly or together will express ORF 2, ORF 3 and ORF 4 proteins in a cell, together with a pharmaceutically acceptable carrier or diluent.

* * * * *